US006248703B1

(12) United States Patent
Finucane et al.

(10) Patent No.: US 6,248,703 B1
(45) Date of Patent: Jun. 19, 2001

(54) EXTRUDED SOAP AND/OR DETERGENT BAR COMPOSITIONS COMPRISING ENCAPSULATED BENEFIT AGENT

(75) Inventors: Kevin Michael Finucane, Saddle Brook, NJ (US); James Joseph Corr, Dix Hills, NY (US); Gregory Alan Ornoski, Cliffside Park; Laurie Ann Coyle, Park Ridge, both of NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/526,073

(22) Filed: Mar. 15, 2000

(51) Int. Cl.[7] ...................................................... A61K 7/50

(52) U.S. Cl. ......................... 510/152; 510/153; 510/155; 510/156

(58) Field of Search .................................... 510/152, 153, 510/141, 142, 155, 156

(56) References Cited

U.S. PATENT DOCUMENTS

| | | | | |
|---|---|---|---|---|
| 5,683,973 | * | 11/1997 | Post et al. | 510/152 |
| 5,795,852 | * | 8/1998 | He et al. | 510/151 |
| 5,965,501 | * | 10/1999 | Rattinger et al. | 510/146 |
| 6,028,042 | * | 2/2000 | Chambers et al. | 510/155 |
| 6,114,291 | * | 9/2000 | He et al. | 510/152 |

* cited by examiner

*Primary Examiner*—Necholus Ogden
(74) *Attorney, Agent, or Firm*—Ronald A. Koatz

(57) ABSTRACT

The invention discloses extruded detergent bars comprising benefit agent containing capsules wherein said capsules are strong enough to withstand extrusion process while still able to release benefit agent upon washing.

7 Claims, No Drawings

EXTRUDED SOAP AND/OR DETERGENT BAR COMPOSITIONS COMPRISING ENCAPSULATED BENEFIT AGENT

FIELD OF THE INVENTION

The present invention relates to extruded soap and/or detergent bars comprising encapsulated benefit agents. Specifically, the bars comprise capsules which are able to survive the extrusion process used in forming the bar, whereupon the consumer is subsequently able to release the encapsulated benefit agent upon use of the products.

BACKGROUND OF THE INVENTION

The controlled or delayed release of a desired benefit agent (e.g., perfume) is itself not new. Thus, in laundry compositions, for example, a perfume may be combined with water soluble polymer; formed into particles; and added to the composition (see U.S. Pat. No. 4,339,356 or 4,209,417 to Whyte). This method, however, works only for powder or granular detergents because as soon as the polymer is hydrated, the perfume is released.

To prevent release of perfume (or other agents) during a liquid wash product is more difficult. The benefit agent must be stable not only in the heat elevated conditions of the wash, but must also be stable against degradation by water and other harsh chemicals in the wash (e.g., bleach, enzymes, surfactant etc.)

One method to provide these benefits is through microencapsulation. In this process, the benefit agent comprises a capsule core coated completely with a material which may be polymeric. U.S. Pat. No. 4,145,184 to Brain et al. and U.S. Pat. No. 4,234,627 to Schilling et al., for example teach use of a tough coating material which prevents diffusion of the benefit agent (e.g., perfume). The perfume is thus delivered to fabric via the microcapsules and is released by moisture such as would occur when fabric is manipulated.

The above microencapsulation patents thus relate to release of a benefit agent (typically perfume) after surviving a washing process (i.e., process in which protection must be heartier).

Applicants are unaware, however, of the use of microencapsulation technology to protect benefit agents (perfume, silicone moisturizer) in personal wash bar compositions, particularly extruded bar compositions. Specifically, whether due to the shear forces applied when the mixed ingredients are typically passed through a screw/mixer; or the extrusion pressure when billets of soap are extruded from the screw/mixer, no capsule materials are known which can survive the soap making process intact with benefit agent inside. Accordingly, no extruded bars comprising microcapsules are known as far as applicants are aware.

U.S. Pat. No. 5,188,753 to Schmidt et al. teaches detergent compositions containing coated perfume particles. The friable capsule coating used to encapsulate the perfume is the same as used in the capsules of the subject invention. U.S. Pat. No. 5,188,753 further teaches that bars containing the coated perfume particles can be formed (see Example IX at column 12 and claim 6)

It is clear from Example IX, however, that it was absolutely not contemplated to use these capsules in a typical bar extrusion process, i.e., one where ingredients are mixed, chilled (to form soap chips), plodded (in a screw), extruded to form logs, cut and stamped. Rather, the composition is prepared by "gently" admixing coated particles into a soap mixture and formed in a bar in a pin die. Thus, clearly, the inventors themselves contemplated that anything other than formation in a pin die would lead to fracturing of the capsules. The Schmidt patent also is a pure soap bar composition soap.

SUMMARY OF THE INVENTION

Unexpectedly, applicants have now found that specific capsule carriers of the invention will survive even a soap bar extrusion process such that core benefit agents inside the capsule will not be released during bar preparation. Moreover, the capsule readily release benefit agent during bar use.

More specifically, the present invention relates to bar compositions comprising a non-water soluble benefit agent core (also called encapsulate fill) surrounded by a friable coating comprising the reaction product of (1) an amine selected from urea and melamine; and (2) an aldehyde selected from formaldehyde, acetaldehyde and glutaraldehyde; and mixtures of said amines and said aldehydes; wherein said capsules are strong enough to survive a soap extrusion process but sufficiently friable to break upon use of the bar by the consumer.

DETAILED DESCRIPTION OF THE INVENTION

The present invention is directed to toilet bar compositions (e.g., pure non-soap compositions or mixtures of soap and non-soap synthetic) which are produced by an extrusion process, i.e., process in which ingredients are mixed, chilled (to form soap chips) and extruded through a plodder to form soap "logs" and which logs are subsequently cut and stamped.

Specifically, applicants have found specific capsules which can be used to deliver benefit agents (perfume, silicone etc.) to the user from the soap bar and which can survive the soap production process. Because of the harshness of the bar production and extrusion process, it has not previously been known how to create a capsule for bars which survives such process.

In general, bars can be classified into one of three categories: (1) soap bars; (2) bars comprising both mostly pure soap and some non-soap actives; and (3) synthetic bars containing little or no soap.

The capsules of the invention are intended for use in categories (2) or (3) defined above.

By "soap" is meant any alkali metal salt or alkanol ammonium salt of aliphatic alkane or alkene monocarboxylic acids. Sodium, potassium, mono-, di- and tri-ethanol ammonium cation or combinations thereof are suitable. In general, sodium soaps are used in the compositions, but from 1 to 25% of soap may be potassium soaps. The soaps useful herein are the well known alkali metal salts of natural or synthetic aliphatic (alkanoic or alkenoic) acids having about 12 to 22 carbon atoms preferably 12 to 18. They may be described as alkali metal carboxylates of acyclic hydrocarbons having about 12 to 22 carbon atoms. A preferred soap is a mixture of about 15% to about 45% coconut oil and about 55% to 85% tallow. The soaps may contain unsaturation in accordance with commercially acceptable standards. Excessive unsaturation is normally avoided.

As noted, the amount of soap used in soap compositions of the present invention is not limited and the invention may be used with compositions having only soap (i.e., no non-soap surfactant), water, preservatives, dyes and other minors; or having no soap at all (non-soap, synthetic detergent bar).

Non-soap detergents (which may comprise all, part or none of the surfactant system) include anionic, nonionic, amphoteric, or cationic detergent actives or mixtures of these.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$RCON(CH_3)CH_2CO_2M,$$

wherein R ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total composition. Preferably, this component is present from about 30% to about 60%.

The acyl isethionate may be an alkoxylated isethionate such as is described in Ilardi et al., U.S. Pat. No. 5,393,466, hereby incorporated by reference. This compound has the general formula:

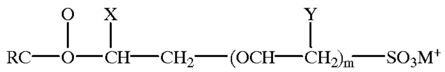

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

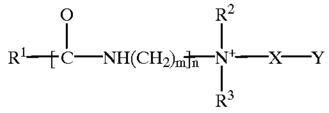

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4;

n is 0 to 1;

X is alkylene of 1 to 3 carbon atoms optionally substituted with hydroxyl, and

Y is $—CO_2—$ or $—SO_3—$

Suitable amphoteric detergents within the above general formula include simple betaines of formula:

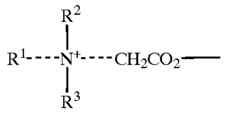

and amido betaines of formula:

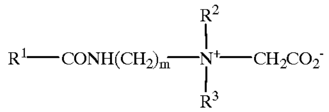

where m is 2 or 3.

In both formulae $R^1$, $R^2$ and $R^3$ are as defined for amphoterics above. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

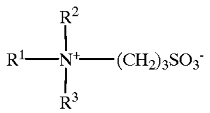

or

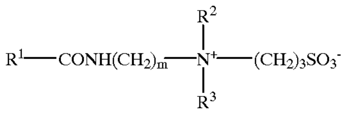

where m is 2 or 3, or variants of these in which $—(CH_2)_3SO_3^-$ is replaced by

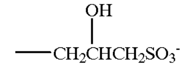

In these formulae $R^1$, $R^2$ and $R^3$ are as discussed previously (R' is $C_7$ to $C_{18}$ alkyl or alkenyl and $R^2$ and $R^3$ are independently alkyl, hydroxyalkyl or carboxyalkyl of 1 to 3 carbons).

The nonionic which may be used as the second component of the invention include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and alkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S Pat. No. 5,009,814 to Kelkenberg, hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

The surfactant (soap, non-soap active or mixture) is generally used in an amount comprising about 20% to about 95% of the bar composition, preferably 40–90% by wt.

In one embodiment of the invention, the surfactant system comprises 30% to 70% by wt. of the composition anionic surfactant, particularly about 40–60% fatty acid isethionate, about 20–30% free fatty acid and 5% to 10% sulfosuccinate; and about 1% to 5% by wt. amphoteric, particularly a betaine (e.g., cocoamidopropylbetaine). The composition also contains about 5–8% electrolyte (i.e., alkali metal isethionate).

In another embodiment, fatty acid isethionate is 30–70% by wt. of composition, about 20–30% free fatty acid and about 5–15% soap. The composition also contains about 3–10% electrolyte (e.g., alkali metal isethionate).

In another embodiment, fatty acid isethionate is 30–70% by wt. composition, about 20–30% by wt. is free fatty acid and about 5–15% soap. The composition also contains about 3–10% electrolyte (e.g., alkali metal isethionate).

In another embodiment of the invention, the surfactant system comprises 40–60% sodium soap 10–30% by wt. fatty acid isethionate (e.g., sodium cocoyl isethionate) and about 7–15% free fatty acid. The composition contains about 3–10% electrolyte (e.g., alkali metal isethionate).

As noted above, however, the invention is in no way limited to the particular type of surfactant system and it is the use of the capsules of the invention in any extruded bar which is the true novelty of the invention. As noted above, however, pure soap bar compositions are not generally contemplated (e.g., because capsule technology is generally too expensive to use in such pure soap compositions).

Another material which may be suitably incorporated into the composition of the invention is water insoluble structurants having a melting point between 40 to 100° C., preferably 50° to 90° C. In particular, materials envisaged include $C_{12}$ to $C_{24}$ fatty acids such as lauric, myristic, palmitic, stearic, arachidonic and behenic acids and mixtures thereof. Sources of these fatty acids are coconut topped coconut, palm, palm kernel, babassu and tallow fatty acids and partially or fully hardened fatty acids or distilled fatty acids. Other suitable water insoluble structurants include $C_8$ to $C_{20}$ alkanols, particularly cetyl alcohol.

Typically, these structurants are used in an amount from about 0% to 40% by wt., preferably 1% to 35% by wt. of the bar composition.

Another optional component which may be suitably used is a water soluble structurant having a melting point of 40° to 100° C., preferably 50° to 90° C.

Suitable materials include moderately high molecular weight polyalkylene oxides, in particular polyethylene glycol or mixtures of polyethylene glycols thereof.

Polyethylene glycols (PEG's) which may be used may have a molecular weight in the range 1,500–10,000. However, in some embodiments of this invention it is preferred to additionally include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% to 1.5% to 4% or 4.5% by weight of the composition. These materials will generally be used jointly with a large quantity of other water soluble structurant (b) such as the above mentioned polyethylene glycol of molecular weight 1,500 to 10,000.

Some polyethylene oxide polypropylene oxide block copolymers melt at temperatures in the required range of 40 to 100° C. and may be used as part or all of the water soluble structurant. Preferred here are block copolymers in which polyethylene oxide provides at least 40% by weight of the block copolymer. Such block copolymers may be used, in mixtures with polyethylene glycol or other water soluble structurant.

The total quantity of water soluble structurant may range from 0% to 50% by weight of the composition, depending on the bar composition.

In one embodiment of the invention, for example, the bar comprises 20–30% isethionate and 30–40% by wt. water soluble structurant (e.g., polyethylene glycol).

Skin mildness improvers also preferably used in the composition of the invention. One example is the salts of isethionate. Effective salts cations may be selected from the group consisting of alkali metal, alkaline earth metal, ammonium, alkyl ammonium and mono-, di- or tri-alkanolammonium ions. Specifically preferred cations include sodium, potassium, lithium, calcium, magnesium, ammonium, triethylammonium, monoethanolammonium, diethanolammonium or triethanolammonium ions.

Particularly preferred as a mildness improver is simple, unsubstituted sodium isethionate.

The skin mildness improver will be present from about 0.5% to about 50%. Preferably, the mildness improver is present from about 1% to about 25%, more preferably from about 2% to about 15%, optimally from 3% to 10%, by weight of the total composition.

Other performance chemicals and adjuncts may be needed with these compositions. The amount of these chemicals and adjuncts may range from about 1% to about 40% by weight of the total composition. For instance, from 2 to 10% of a suds-boosting detergent salt may be incorporated. Illustrative of this type additive are salts selected from the group consisting of alkali metal and organic amine higher aliphatic fatty alcohol sulfates, alkyl aryl sulfonates, and the higher aliphatic fatty acid taurinates.

Adjunct materials including germicides, perfumes, colorants and pigments such as titanium dioxide and preservatives may also be present.

Water should be present at 1–30% by weight of the composition, preferably 2 to 20% by wt., most preferably 3 to 15% or 3 to 12% by wt.

CAPSULES AND BENEFITS AGENTS

As noted above, the key to the invention resides in the fact that applicants have unexpectedly found a capsule composition which can survive the extrusion process whereby toilet bars are made (i.e., without prematurely releasing benefit agents inside the capsules). The capsules, however, are sufficiently friable that they will break up when used by the consumer during wash. Thus, the ingredient is only released when the user is actually using the soap and the benefit agent is only gradually consumed over the various times that the consumer uses the bar.

Benefit agents in the context of the instant invention are materials that have the potential to provide a positive and often longer term effect to the substrate being cleaned, e.g., to the skin. Skin benefit agents suitable for this invention are water insoluble materials that can protect, moisturize or condition the skin after being deposited from the bar cleansing composition.

Preferred benefit agents include:

a) silicone oils, gums and modifications thereof such as linear and cyclic polydimethylsiloxanes; amino, alkyl alkylaryl and aryl silicone oils;

b) fats and oils including natural fats and oils such as jojoba, soybean, sunflower, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;

c) waxes such as carnauba, spermaceti, beeswax, lanolin and derivatives thereof;

d) hydrophobic plant extracts;

e) hydrocarbons such as liquid paraffins, petrolatum, microcrystalline wax, ceresin, squalene, squalane, pristan and mineral oil;

f) higher fatty acids such as lauric, myristic, palmitic, stearic, behenic, oleic, linoleic linolenic, lanolic, isostearic and poly unsaturated fatty acids (PUFA) acids;

g) higher alcohols such as lauryl, cetyl, styrol, oleyl, behenyl, cholesterol and 2-hexadecanol alcohol;

h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester sorbitol ester and the like;

i) essential oils such as fish oils, mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, Citronelle, borneol, linalool, geraniol, evening primrose, camphor, thymol, spirantol, pinene, limonene and terpenoid oils;

j) lipids and lipid like substance such as cholesterol, cholesterol ester ceramides, sucrose esters and pseudoceramides as described in European Patent Specification No. 556 957;

k) vitamins such as vitamin A and E, and vitamin alkyl esters, including vitamin C alkyl esters;

l) sunscreens such as octyl methoxyl cinnamate (Parsol MCX) and butyl methoxy benzoylmethane (Parsol 1789);

m) Phospholipids such as lecithins;

n) antimicrobial such as 2-hydroxy-4,2',4'-trichlorodiphenylether (DP300) and 3,4,4'-trichlorocarbanilide (TCC); and mixtures of any of the foregoing components.

The benefit agent could be used alone or it could be dispersed in a polymer or copolymer.

The benefit agent is encapsulated to provide a friable coating which prevent the benefit agent from diffusing throughout the bar composition.

The coating materials used herein are friable, and are designed to break-up as the benefit agent is used, thereby releasing the benefit agent.

The agent may be coated with more than one friable coating material to produce a more than one layer of coating. Different coating materials can be chosen to provide different protection as needed, so long as one of the coatings, generally, the outermost, is friable.

The individual benefit agent particles may also be agglomerated with the coating material to provide larger particles which comprise a number of the individual benefit agent particles. This agglomerating material surrounding the particles provides an additional barrier to diffusion of the agent out of the particles. Such an approach also minimizes the surface area of free particles susceptible to diffusion. The ratio of particles to agglomerate material will vary greatly depending upon the extent of additional protection desired. This agglomeration approach may be particularly useful with benefit agents (e.g., perfumes) that are especially susceptible to degradation. Also, agglomeration of very small benefit agents particles would provide additional protection against premature diffusion out of benefit agents.

In preferred embodiments of the invention the capsule should be below 100: more preferably below 60:.

Encapsulation Process

For friable coatings, the process of manufacture is based on applying the coating as a kind of "shell" to the particles. For benefit agent particles whose carrier material has a melting point below that of the boiling point of the solvent used in the process, the process involves melting the carrier and benefit agent together and adding the molten mixture to a solvent solution of the "shell" material, or a suitable precursor, held above the carrier melting temperature. The system is agitated sufficiently to form an emulsion of the carrier/perfume of desired liquid drop size in the shell solution. The conditions necessary to deposit the encapsulating material are then established and the whole is cooled to give encapsulated solid particles having the desired, friable "shell". Water insolubility of the shell is established either at the deposition stage, or by suitable treatment prior to isolation or use of the particles.

Although the process described here is a one step molten drop formation/encapsulating procedure, it should be readily apparent to those skilled in the art that encapsulation of pre-formed particles can be accomplished in a like manner. The pre-formed particles can be prepared in a variety of ways, including cryo grinding, spray drying, spray congealing and meltable dispersion techniques such as those described in books by P. B. Deasy ("Microencapsulation & Related Dry Processes", Dekker, N.Y., 1986) and A. Kondo ("Microcapsule Processing and Technology", Dekker, N.Y. 1979). Such techniques would be required for carrier materials having a melting point above the solvent boiling point.

A variety of suitable encapsulating procedures can be used, such as reviewed in the books by Deary and Kondo above. Depending on materials used, the shell can impart hydrophilicity or hydrophobicity to the particles. Non-limiting examples of encapsulating materials and processes include gelatin-gum arabic concentrate deposited by a complex coacervation procedure, e.g., U.S. Pat. No. 2,800,457, for hydrophilic shells, and urea formaldehyde deposited by a polycondensation process, e.g., U.S. Pat. No. 3,516,941, for hydrophobic shells.

Water insolubility of the shell materials may be imparted by cross-linking of the gelatin-gum arabic coacervate with suitable aldehydes or other known gelatin hardeners after deposition. Polymerization of the urea formaldehyde precondensate during the encapsulation process yields water-insolubility.

The slurry containing the benefit agent particles can be used directly, e.g., spray dried with other components of the formulation, or the particles can be washed and separated, and dried if desired.

As noted previously, the capsules themselves are made from reaction product of:

(1) an amine selected from urea and melamine or mixtures thereof; and (2) an aldehyde selected from the group consisting of formaldehyde, acetaldehyde, glytamaldehyde and mixtures thereof.

The capsules are strong enough to survive soap extrusion but sufficiently friable to break upon use by consumer.

The capsules are preferably less than 300μ in size, preferably less than 100μ.

Bar Processing

Initially, the components of the bar formulation should be intimately mixed (without the capsulate being present). This can be accomplished by mixing the components in an aqueous slurry, typically using 6 to 15% water (94–85% solids) from 100° C. to 200° C.

The slurry can be drum-dried to a moisture content up to 9% in the dry mix. Alternatively, the components can be mixed dry, preferably in a mechanical mixer such as a Werner-Pfleiderer or Day mixer. At 85° C. (185° F.), a few hours of mixing may be necessary to dry the mixture to the desired moisture, while at 115° C. (240° F.), a smooth blend will be obtained in approximately one half hour. The time can be reduced by further increasing the temperature, which will of course be kept below a temperature at which any of the components would be degraded. All of the components can be added together, or it may be desirable to mix the lathering detergent with an amount of water first and then incorporate the other ingredients.

After the components have been mixed, the composition is cooled and solidified, typically using a chilled flaker, to form small chips. The chips are mixed with perfume and color and the encapsulate (with benefit agent) is added at this point. The perfumed product with encapsulated benefit agent is transferred to the packing floor and extruded in the form of billets.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Example 1

Silicone was added to the following compositions:

| Component | % by Wt. |
|---|---|
| Acyl isethionate | About 40–60% |
| Free fatty acid | 20–30% |
| Soap | 5–15% |
| Sodium isethionate | 3–10% |
| Other (perfume, water) | To balance |

Results were as follows:

| | Composition I | Composition I | Composition I |
|---|---|---|---|
| Silicone | None Added (Comparative) | 5% DC 200 60,000 CST Oil | 3.8% DC 200 60,000 CST Oil |
| Method of Addition | — | Free Silicone Oil | 150 Micron Encapsulates w/ 70% 60,000 CPS Oil & 30% DC 245 Fluid |
| Deposition (μgram/cm$^2$ | 0.0 | <0.2 | 0.83 |

The above Table clearly shows that capsule addition (last column) significantly enhances silicone deposition (i.e., >400% increase).

Measurement of silicone was conducted as follows:

A piece of bar was rubbed on a prewetted (25 ml water) young porcine skin (58.1 cm$^2$) for 15 sec. After rinsing the skin under tap water at 28–30° C. for 15 sec, it was patted dry with paper towel, and air dried for 2 minutes. The skin was then placed in a jar and a known weight of xylenes was added (~24–28 g). The extract was then removed and the silicone content was determined using a Thermo Jarrell Ash Atom Scan -25 Inductively Coupled Plasma Spectrophotometer.

Example 2

Incorporation of emollient capsules and deposition of emollient can also be measured from the following compositions:

| Component | % by wt. |
|---|---|
| Soap | About 50% |
| Coco fatty acid isethionate | About 20% |
| Sodium isethionate | About 6% |
| Fatty acid | About 95 |
| Other (perfume, water etc.) | About 15% |
| Fatty acid isethionate | About 50% |
| Free fatty acid | About 25% |
| Free isethionate | About 5.5% |
| Sulfosuccinate* | About 6.0% |
| Betaine** | About 2.0% |
| Preservative, dye, water and other minors | Balance |

*Cocoamido sulfosuccinate
**Cocoamidopropyl betaine

What is claimed is:

1. An extruded detergent bar composition comprising:

(a) 20% to 95% by wt. soap or non-soap active selected from the group consisting of anionic surfactants, nonionic surfactants, amphoteric surfactants, cationic surfactants and mixtures thereof, wherein soap cannot be the only active;

(b) 0 to 40% by wt. $C_8$ to $C_{22}$ free fatty acid;

(c) 0 to 50% water soluble structurant having melting point of from about 40° to 100° C.;

(d) 0 to 40% by wt toilet bar adjuvants selected from the group consisting of perfumes, pigments, preservatives, electrolyte salts and mixtures thereof;

(e) 1% to 30% by wt. water; and (f) 0.5% to 20% by wt. encapsulates which comprise about 0.25% to 50% of benefit agent;

wherein said encapsulate is a friable coating and wherein said friable coating is the reaction product of (1) an amine selected from the group consisting of urea, melamine and mixtures thereof; and (2) an aldehyde selected form the group consisting formaldehyde, acetaldehyde glutaraldehyde and mixtures thereof;

wherein said bar is formed by:

(a) mixing components of bar composition without capsulate being present at temperature of about 85° C and higher;

(b) cooling to form chips;

(c) adding encapsulate; and (d) extruding to form billets.

2. A composition according to claim 1, comprising 5–30% free fatty acid.

3. A composition according to claim 1, wherein structurant is polyalkylene glycol.

4. A composition according to claim 1, wherein electrolyte (d) is alkali metal isethionate.

5. A composition according to claim 4, wherein alkali metal isethionate comprises 3–10% of composition.

6. A composition according to claim 1, wherein capsules are less than 300 microns.

7. A composition according to claim 6, wherein capsules are less than 100$\mu$ in size.

* * * * *